United States Patent

Narayan et al.

[11] Patent Number: 5,912,381
[45] Date of Patent: Jun. 15, 1999

[54] POLYESTER OLIGOMER ACRYLATES

[75] Inventors: Ramesh Narayan, Bensalem; Miguel A. Dones, Hatfield, both of Pa.; Michael McDermott, Rocky River, Ohio

[73] Assignee: Henkel Corporation, Gulph Mills, Pa.

[21] Appl. No.: 08/733,682

[22] Filed: Oct. 17, 1996

Related U.S. Application Data

[63] Continuation-in-part of application No. 08/706,633, Sep. 6, 1996.

[51] Int. Cl.$^6$ .................................................. C07C 69/76
[52] U.S. Cl. ....................................................... 560/81
[58] Field of Search ................... 560/91, 95, 81

[56] References Cited

U.S. PATENT DOCUMENTS

| | | | |
|---|---|---|---|
| 2,736,609 | 2/1956 | Vinal | 300/2 |
| 3,919,172 | 11/1975 | Rhein et al. | 260/75 R |
| 4,382,135 | 5/1983 | Sinka et al. | 526/301 |
| 4,522,465 | 6/1985 | Bishop et al. | 350/96.3 |
| 4,581,407 | 4/1986 | Schmid | 524/548 |
| 4,935,535 | 6/1990 | Chiang et al. | 560/26 |
| 5,000,758 | 3/1991 | Baillargeon et al. | 44/399 |
| 5,320,886 | 6/1994 | Bowen | 428/34.1 |

FOREIGN PATENT DOCUMENTS 58-140048  8/1983  Japan .

OTHER PUBLICATIONS

"Coatings", Encyclopedia of Polymer Science & Engineering, supp. vol., pp. 109–110 (John Wiley & Sons, NY, NY, 1989).

*Primary Examiner*—Jeffrey Smith
*Assistant Examiner*—Wu C. Cheng
*Attorney, Agent, or Firm*—Ernest G. Szoke; Wayne C. Jaeschke; Glenn E. J. Murphy

[57] ABSTRACT

A compound having the formula:

$$((CH_2=CR^1-C(O)O-)_xR^2-(O-C(O)R^3)_y-O-C(O))_n-R^4-(C(O)OM)_m$$

wherein:
$R^1$ is hydrogen or methyl,
$R^2$ is an alkylene group or substituted alkylene group (typically having less than six carbon atoms, more typically two or three carbon atoms),
$R^3$ is an alkylene group or substituted alkylene group (typically having less than ten carbon atoms, more typically from four to six carbon atoms),
$R^4$ is an aromatic radical (e.g. the residue of an aromatic polycarboxylic polyanhydride having a functionality of one half the sum of n and m),
n and m are integers from two to four (typically two or three),
x is an integer from one to three, and
y is an integer from one to five.
Among the compounds which fall within the above formula are those in which $R^1$ is hydrogen, $R^2$ is an ethylene group, $R^3$ is a pentamethylene group, and $R^4$ is the residue of benzene tetracarboxylic dianhydride or benzophenone tetracarboxylic dianhydride, n and m are each two, x is one, and y is two. This invention also relates to a polymerizable composition comprising a compound as set forth above and to a method of coating a substrate comprising polymerizing a composition comprised of the compound set forth above while in contact with a substrate.

19 Claims, No Drawings

POLYESTER OLIGOMER ACRYLATES

CROSS-REFERENCE TO RELATED APPLICATIONS

This application is a continuation-in-part of U.S. Ser. No. 08/706,633, filed Sep. 6, 1996, the disclosure of which is incorporated herein by reference.

FIELD OF THE INVENTION

The present invention relates to radiation curable polyester oligomers, to polymerizable compositions, and to methods of coating.

BACKGROUND OF THE INVENTION

The technology for the production of radiation curable coatings using acrylate-functional oligomers is known. The article "Coatings", Encyclopedia of Polymer Science and Engineering, supp. vol., p. 109 and 110 (John Wiley & Sons, Inc. N.Y., N.Y., 1989) notes the most widely used vehicle systems are oligomers substituted with multiple acrylate ester groups mixed with low molecular weight monofunctional, difunctional, or trifunctional acrylate monomers.

U.S. Pat. No. 4,522,465 (Bishop, et. al.) discloses buffer-coated and overcoated optical glass fiber in which the topcoat has the high strength and high tensile modulus combined with good elongation and solvent resistance associated with extruded jacket coatings, but which is applied by ordinary coating procedures and cured by exposure to ultraviolet radiation. The coating compositions comprise 30% to about 80% of linear diethylenic polyester polyurethanes which are the linear polyurethane reaction product of an organic diisocyanate with hydroxy-functional polyester formed by reacting a diol, such as ethylene glycol, with certain dicarboxylic acids, such as adipic acid. This polyurethane is end capped with a monoethylenically unsaturated monohydric alcohol, e.g. the hydroxy-functional acrylate of caprolactone dimer derived from caprolactone and 2-hydroxyethyl acrylate supplied by Union Carbide Corporation under the designation Tone M-100.

U.S. Pat. No. 4,581,407 (Schmid) discloses an essentially isocyanate-free polyurethane polyurea polyethylenic oligomer which is unusually strong and elastic and is thus useful as a binder for a coating containing a magnetic pigment. This oligomer is the reaction product of: (1) organic diisocyanate; (2) a stoichiometric deficiency of difunctional materials reactive therewith and consisting essentially of: (A) polyoxyalkylene glycol having a molecular weight of from 200 to 1000; (B) dihydric bisphenol-based alkylene oxide adduct containing from 2–10 alkylene groups per molecule; and (C) polyoxyalkylene diprimary amine having a molecular weight of from 150 to 800. In all of these, the alkylene groups contain from 2–4 carbon atoms. The polyurethane polyurea so-constituted is capped with monohydric ethylenic compound, such as the adduct of caprolactone dimer and 2-hydroxyethyl acrylate, to provide a molecular weight in the range of about 5,000 to about 30,000. This polyethylenic oligomer is cured by radiation exposure, such as an electron beam, using from 5% to 25%, based on total polymer solids, of polyethylenic polyhydroxyalkyl melamine.

SUMMARY OF THE INVENTION

This invention relates to a compound having the formula:

$$(((CH_2=CR^1-C(O)O-)_x R^2-(O-C(O)R^3-)_y-O-C(O))_n-R^4-(C(O)OM)_m$$

wherein:
$R^1$ is hydrogen or methyl,
$R^2$ is an alkylene group or substituted alkylene group (typically having less than six carbon atoms, more typically two or three carbon atoms),
$R^3$ is an alkylene group or substituted alkylene group (typically having less than ten carbon atoms, more typically from four to six carbon atoms),
$R^4$ is an aromatic radical (e.g. the residue of an aromatic polycarboxylic polyanhydride having a functionality of one-half the sum of n and m),
M is hydrogen or a counter-ion of a salt of said compound,
n and m are integers from two to four (typically two or three),
x is an integer from one to three, and
y is an integer from one to five.

This invention also relates to a polymerizable composition comprising a compound as set forth above and to a method of coating a substrate comprising polymerizing a composition comprised of the compound set forth above while in contact with a substrate.

Among the compounds which fall within the above formula are those in which $R^1$ is hydrogen, $R^2$ is an ethylene group, $R^3$ is a pentamethylene group, and $R^4$ is the residue of benzene tetracarboxylic dianhydride or benzophenone tetracarboxylic dianhydride, n and m are each two, x is one, and y is two. The compound is preferably in the form of the free acid, i.e. wherein each M is hydrogen, but may be in the form of a salt of said compound, i.e. M can be an alkali, alkaline earth or ammonium ion.

Broadly speaking, this oligomer is prepared by forming a mixture of an acrylate- or methacrylate-functional and mono-hydroxyl-functional polyester oligomer and polycarboxylic polyanhydride. These two components of the mixture then react in the presence of an esterification catalyst. The resulting product typically contains multiple ester and carboxylate functionality with the ester and carboxylate functionality being essentially equal. Further, it is preferred to use an equivalent ratio of anhydride:hydroxyl-functional acrylate of roughly 1:1. Thus, the predominant product of the reaction should be the product of "opening" each anhydride to form a diester/diacid product. However, the reaction product will typically be a complex mixture which is further comprised of residual hydroxy-functional acrylate.

DETAILED DESCRIPTION OF THE INVENTION

The olefinically unsaturated compounds employed for the preparation of the present acryloester oligomers may be monomeric or polymeric and are characterized by the presence of a single dicarboxylic anhydride-reactive moiety such as an active hydrogen group, e.g. a hydroxyl group. Preferably, the single active hydrogen group is a hydroxyl group. Illustrative of unsaturated addition-polymerizable monomeric organic compounds having a single dicarboxylic anhydride-reactive active hydrogen group are 2-hydroxyethyl acrylate, 2-hydroxyethyl methacrylate, 2-hydroxypropyl acrylate, 2-hydroxypropyl methacrylate, pentaerythritol triacrylate, N-hydroxymethyl acrylamide, N-hydroxymethyl methacrylamide, diethylene glycol monoacrylate, diethylene glycol monomethacrylate, glycerine dimethacrylate, trimethylol propane dimethacrylate, reaction products of polyether glycols of acrylic or methacrylic acid and the like.

The preferred olefinically unsaturated compounds are lactone-modified acrylate or methacrylate acid esters (hereinafter "lactone-acrylate adducts") prepared by reacting an appropriate lactone with an acrylate or methacrylate acid ester.

Lactones employed in the preparation of the lactone-acrylate adducts typically have the formula:

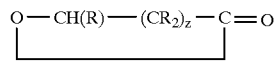

wherein R is hydrogen or an alkyl group having from 1 to 12 carbon atoms, z is from 4 to 7 and at least (z−2) of the R's is hydrogen. Preferred lactones are the epsilon-caprolactones wherein z is 4 and at least 6 of the R's are hydrogen with the remainder, if any, being alkyl groups. Preferably, none of the substituents contain more than 12 carbon atoms and the total number of carbon atoms in these substituents on the lactone ring does not exceed 12. Unsubstituted epsilon-caprolactone, i.e., where each R is hydrogen, is a derivative of 6-hydroxyhexanoic acid. Both the unsubstituted and substituted epsilon-caprolactones are available by reacting the corresponding cyclohexanone with an oxidizing agent such as peracetic acid.

Substituted epsilon-caprolactones found to be most suitable for preparing the present lactone-acrylate adducts are the various epsilon-monoalkylcaprolactones wherein the alkyl groups contain from 1 to 12 carbon atoms, e.g., epsilon-methyl-caprolactone, epsilon-ethyl-caprolactone, epsilon-propyl-caprolactone and epsilon-dodecyl-caprolactone. Useful also are the epsilon-dialkylcaprolactones in which the two alkyl groups are substituted on the same or different carbon atoms, but not both on the omega carbon atoms. Also useful are the epsilon-trialkylcaprolactones wherein 2 or 3 carbon atoms in the lactone ring are substituted provided, though, that the omega carbon atom is not di-substituted. The most preferred lactone starting reactant is the epsilon-caprolactone wherein z in the lactone formula is 4 and each R is hydrogen.

The acrylate or methacrylate acid esters utilized to prepare the lactone-acrylate adducts contain from 1 to 3 acrylyl or alpha-substituted acrylyl groups and one or two hydroxyl groups. Such esters are commercially available and/or can be readily synthesized. Commercially available esters include the hydroxyalkyl acrylates or hydroxyalkyl methacrylates wherein the alkyl group contains from 2 to 10 carbon atoms, preferably from 2 to 6 carbon atoms. The hydroxyalkyl acrylates and methacrylates have the following formula:

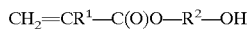

wherein $R^1$ is hydrogen or methyl and $R^2$ is a linear or a branched alkylene group having from 2 to 10 carbon atoms, preferably from 2 to 6 carbon atoms.

Examples of suitable hydroxyalkyl acrylates and methacrylates include 2-hydroxyethyl acrylate, 2-hydroxypropyl acrylate, 3-hydroxypropyl acrylate, 2-hydroxybutyl acrylate, 4-hydroxybutyl acrylate, 3-hydroxypentyl acrylate, 6-hydroxynonyl acrylate, 2-hydroxyethyl methacrylate, 2-hydroxypropyl methacrylate, 3-hydroxypropyl methacrylate, 2-hydroxybutyl methacrylate, 2-hydroxypentyl methacrylate, 5-hydroxypentyl methacrylate, 7-hydroxyheptyl methacrylate and 5-hydroxydecyl methacrylate.

Preferred lactone-acrylate adducts have the formula:

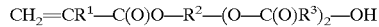

wherein $R^1$, $R^2$, and $R^3$ are as described above.

The lactone-acrylate adduct is prepared by reacting the lactone with the hydroxyalkyl acrylate in the presence of less than about 200 parts per million of a catalyst. The catalysts which may be used include one or more organometallic compounds and other metallic compounds such as stannic chloride or ferric chloride and other Lewis or protonic acids. Preferred catalysts include stannous octoate, dibutyltin dilaurate, and other tin compounds; titanates such as tetraisopropyl titanate and butyl titanate; and the like.

The reaction is carried out at a temperature of from about 100° C. to about 400° C., preferably from about 120° C. to about 130° C. The reaction may be carried out at atmospheric pressure, although higher or lower pressures may be used. The reaction is generally carried out in the presence of oxygen to inhibit polymerization of the hydroxyalkyl acrylate. The reaction is generally carried out for a period of from about 2 to about 20 hours. The reaction is carried out in the presence of a suitable inhibitor to prevent polymerization of the hydroxyalkyl acrylate double bond. These inhibitors include the monomethyl ether of hydroquinone, benzoquinone, phenothiazine, methyl hydroquinone, 2,5-di-t-butylquinone, hydroquinone, benzoquinone and other common free radical inhibitors known in the art. The level of inhibitor used is less than 1000 parts per million, preferably less than 800 parts per million, and most preferably, less than 600 parts per million. A molar ratio of the lactone to hydroxyl groups in the ester of from about 1:0.1 to about 1:5, preferably from about 1:0.3 to about 1:3 is typically utilized.

An example of a lactone-acrylate adduct preferred for use in the present invention is a caprolactone-2-hydroxyethyl acrylate adduct supplied by Union Carbide Corporation under the tradename TONE M-100, which has the formula

A polycarboxylic polyanhydride aromatic compound is reacted with the lactone-acrylate adduct to introduce the ester and free carboxylate functionalities into the compound. The $R^4$ is thus an aromatic radical. Typically, $R^4$ will contain from about 6 to about 36 carbon atoms, more typically from about 6 to about 13 carbon atoms. $R^4$ will typically be a hydrocarbon group or a heterocyclic group. $R^4$ is preferably selected from the group consisting of phenyl, substituted phenyl, phenonyl (i.e. a phenyl group bearing a ketone substituent), and substituted phenonyl (e.g. benzophenonyl). In preferred embodiments, $R^4$ contains an aromatic ketone functionality, e.g. a benzophenone group or an acetophenone group.

Suitable polycarboxylic polyanhydride aromatic compounds preferably contain on average 2 to at most 4 anhydride groups. Examples of suitable such compounds are benzene tetracarboxylic dianhydride or benzophenone tetracarboxylic dianhydride.

For reaction with the polycarboxylic polyanhydride aromatic compound, a mixture thereof with the lactone-acrylate adduct is typically heated to a temperature of about from 40 to 150° C. and typically about 80° C., in the presence of a catalytic amount of an esterification catalyst, preferably a tertiary amine, e.g. an aromatic amine such as dimethylamino-pyridine or a tri-alkyl amine, e.g. triethylamine. The amount of the anhydride equivalents of polycarboxylic polyanhydride aromatic compound will be essentially equal (e.g. 1.01:1 to 1:1.01), on an equivalents basis, to the hydroxyl equivalents of the lactone-acrylate adduct. This will produce a product which is predominantly comprised of molecules wherein the ester and free carboxylate functionality is equal.

The reaction is allowed to exotherm and is then typically heated, e.g. to a temperature of about 100° C. to about 140° C., more typically about 120° C. to about 140° C., and held for about from 10 minutes to about 2 hours more typically about 20 minutes to one hour, until the theoretical anhydride content is <0.5% by weight as calculated, for example, from the measured acid value of the product or by spectroscopic methods (e.g. Fourier Transform Infra-Red spectroscopy), the total reaction time typically being about 30 minutes to about 4 hours, more typically from about one to about two hours. Thereafter, the product is cooled prior to storage.

The reaction with the polycarboxylic polyanhydride aromatic compound is usually carried out at moderate temperature in the presence of a catalyst which promotes the ester-forming reaction, such as dimethylamino-pyridine. The order of reaction is largely immaterial, it being possible to bring in the monohydric ethylenic compound either at the beginning, during the middle of the procedure, or as the last reactant. All of these variations are known in the art. It is usual herein to employ the polycarboxylic polyanhydride aromatic compound and the materials reactive therewith in stoichiometric amounts and to continue the reaction until the anhydride functionality is substantially undetectable. As will be understood, these reactions are conveniently carried out neat with reactants that are liquid at the reaction temperature or in solvent solution.

The reaction is generally carried out in the presence of oxygen to inhibit polymerization of the acrylate or methacrylate functionality. The reaction is preferably carried out in the presence of a suitable inhibitor to prevent polymerization of the acrylate or methacrylate double bond. These inhibitors include the monomethyl ether of hydroquinone, benzoquinone, phenothiazine, methyl hydroquinone, 2,5-di-t-butylquinone, hydroquinone, benzoquinone and other common free radical inhibitors known in the art. The level of inhibitor used is less than 1000 parts per million, preferably less than 800 parts per million, and most preferably, less than 600 parts per million.

The compound is preferably in the form of the free acid, i.e. wherein each M is hydrogen, but may be in the form of a salt of said compound, i.e. M can be an alkali, alkaline earth or ammonium ion. Neutralization of the free acid form of the compound with a suitable base to introduce an M counter-ion can be accomplished if desired.

The compound of the present invention can be applied to a variety of substrates. These include, for example, porous stock such as paper and cardboard, wood and wood products, metals such as aluminum, copper, steel, and plastics such as P.V.C., polycarbonates, acrylic and the like. After addition of a suitable photoinitiator, e.g., PHOTOMER 51® brand photoinitiator (benzyl dimethyl ketal), the compound is applied by methods such as spraying, rollcoating, flexo and gravure processes onto a selected substrate. The resulting coated substrate, e.g., a paper, is typically cured under a UV or electron beam radiation. The compound may optionally be mixed with other substances such as pigments, resins, monomers and additives such as anti-oxidants and rheological modifiers. It is an advantage of certain embodiments of this invention that improved adhesion to substrates, e.g. aluminum, steel, polyethylene terephthalate, and Mylar, is exhibited by such compounds of the invention as compared to compositions wherein none of the monomers contain a free carboxyl group or salt thereof.

The compound of this invention may also be formulated with other polymerizable components to form a polymerizable mixture. Typical examples of suitable monomers which can be used as a reactive diluent, are the vinyl or vinylidene monomers containing ethylenic unsaturation, and which can copolymerize with the compositions of this invention are aromatic monomers such as styrene, vinyl toluene, tertiary butyl styrene, alpha-methyl-styrene, monochlorostyrene, dichlorostyrene, divinylbenzene, ethyl vinyl benzene, diisopropenyl benzene, acrylate or methacrylate esters such as methyl acrylate, ethyl acrylate, methyl methacrylate, ethyl methacrylate, hexanediol diacrylate, nitriles such as acrylonitrile, methacrylonitrile, the vinyl esters, such as vinyl acetate and the monovinyl esters of saturated and unsaturated aliphatic, monobasic and polybasic acids, such as the vinyl esters of the following acids: propionic, isobutyric, caproic, oleic, stearic, acrylic, methacrylic, crotonic, succinic, maleic, fumaric, itaconic hexahydrobenzoic, citric, tartaric, etc., as well as the corresponding allyl, methallyl, etc., esters of the aforementioned acids, the itaconic acid monoesters and diesters, such as the methyl, ethyl, butyl esters, etc.; the maleic and fumaric acid monoesters, diesters and their amide and nitrile compounds, such as diethyl maleate, maleyl tetramethyl diamide, fumaryl dinitrile, dimethyl fumarate; cyanuric acid derivatives having at least one copolymerizable unsaturated group attached directly or indirectly to the triazine ring such as diallyl ethyl cyanurate, triallyl cyanurate, etc., ethers such as vinyl allyl ether, divinyl ether, diallyl ether, resorcinol divinyl ether, etc., diallyl chlorendate, diallyl tetrachloro phthalate, diallyl tetrabromophthalate, dibromopropargyl acrylate, as well as the partial fusible or soluble polymerizable polymers of the hereinabove listed monomers, etc. Preferred reactive diluents are the adducts of on average 1 to 3 moles of ethylene oxide and/or propylene oxide with an alkanediol, typically on average 1.5 moles to 2.5 moles, and more typically on average 1.8 to 2.2 moles, which have been reacted with a stoichiometric amount of acrylic acid, or a reactive derivative thereof, and/or methacrylic acid or a reactive derivative thereof. The hexanediol 2EO adducts are particularly preferred, this adduct having on average 1.9 to 2.1 moles of ethylene oxide. In this adduct, the predominant molecular species will contain two ethoxylate residues. Thus, the average degree of ethoxylation per hydroxyl group of the alkanetriol will be about 1. Examples of such diluents are disclosed in U.S. Pat. No. 4,382,135, the disclosure of which is incorporated herein by reference.

In preparing the polymerizable compositions of this invention containing the reaction product of this invention and one or more of the monomers of the type listed hereinabove, the relative amount of the monomers can vary broadly. In general, however, the monomer or monomers are used at less than about 50% by weight of the composition, typically in the range of about 10% to about 30% by weight, and more typically in the range of about 15% to about 25% by weight.

The new derivatives of this invention can be cured or converted to the infusible state, alone or in admixture with other monomers or polymers by exposure to radiation alone or in the presence of radical generating catalysts such as benzoin, benzoin ethers, and Michler's Ketone. The free radical initiator is typically present at from about 0.01 to about 20% by weight of the radiation curable components. Examples of useful radiation include ultraviolet light and ionizing radiation such as generated by X-Ray machines; electron accelerators such as van der Graaf machines, travelling wave linear accelerators, particularly of the type described in U.S. Pat. No. 2,736,609, natural and synthetic radioactive material, for example cobalt 60, etc. To ensure that the composition does not prematurely polymerize, a free radical inhibitor may be added to the polymerizable composition. Examples of suitable inhibitors include hydroquinone and the methyl ether thereof or butylated hydroxy toluene at a level of from about 5 ppm to about 2000 ppm by weight of the polymerizable components. Additives which are particularly useful in prolonging the shelf-life of the composition can also be used, e.g. ultra-violet stabilizers such as Florstab UV-II from Kromachem.

The compositions of this invention are useful in the preparation of molded, cast, laminated and coated products as adhesives, impregnants and protective coatings. They can be used alone or with fillers, dyes, pigments, opacifiers, lubricants, plasticizers, natural or synthetic resins or other modifying bodies.

In the method of coating a substrate according to the invention, the composition, optionally containing a photoinitiator, is applied to the surface of a substrate and subsequently exposed to a radiation source until an adherent dry polymerized film is formed on the substrate. Sources of radiant energy appropriate for initiating cure of the formulations have been described extensively in the literature and are well known to those skilled in the art. These include various sources of particulate and non-particulate radiation producing wavelengths generally less than 700 nanometers. Especially useful is actinic radiation in the 180–440 nm range which can be conveniently obtained by use of one of several commercially available ultra-violet sources specifically intended for this purpose. These include low, medium and high pressure mercury vapor lamps, He—Cd and Ar lasers, xenon arc lamps, etc. Photoinitiator systems having a corresponding sensitivity to light in this wave band are normally incorporated into the formulation and upon irradiation lead to the formation of reactive species capable of initiating free radical polymerization. Similarly, free radical polymerization may be induced by exposure of the formulation to an electron beam without the use of a photoinitiator. Equipment capable of generating a curtain of electrons with energies between 150 and 300 KeV is particularly suitable for this purpose and its use is well documented in the literature.

Particularly preferred sources of radiation emit electromagnetic radiation predominantly in the ultra-violet band. When such a source is used, the polymerizable composition preferably contains a photoinitiator susceptible to ultra-violet radiation, e.g. benzoin, benzoin ethers, alpha, alpha-dimethoxy-alpha-phenylacetophenone, diethoxyacetophenone, alpha-hydroxy-alpha, alpha-dimethylacetophenone, and 1-benzoylcyclohexanol.

The amount of radiation necessary to cure the composition will of course depend on the angle of exposure to the radiation, the thickness of the coating to be applied, and the amount of polymerizable groups in the coating composition, as well as the presence or absence of a free radical initiating catalyst. For any given composition, experimentation to determine the amount of radiation sensitive pi bonds not cured following exposure to the radiation source is the best method of determining the amount and duration of the radiation required. Typically, an ultra-violet source with a wavelength between 200 and 420 nm (e.g. a filtered mercury arc lamp) is directed at coated surfaces carried on a conveyor system which provides a rate of passage past the ultra-violet source appropriate for the radiation absorption profile of the composition (which profile is influenced by the degree of cure desired, the thickness of the coating to be cured, and the rate of polymerization of the composition).

The composition is useful for placement on a wide range of substrates including paper, rigid and flexible plastics, metallic substrates, cement, glass, asbestos products, wood and the like. Examples of formulation categories include, but are not limited to, the following: overprint varnishes for paper and board; lithographic, screen, letterpress, flexographic, and gravure printing inks; stereolithography baths; pressure-sensitive and assembly adhesives; vinyl floor coatings; pigmented and unpigmented wood finishes; coatings for optical fiber; waterborne spray-applied coatings; base and top coatings for rigid and flexible plastics; etch and solder photomasks.

A preferred use of the polymerizable compositions of this invention is in the formulation of radiation curable inks. When formulated into an ink, the polymerizable composition of the reaction product and diluent can be a major proportion or a minor proportion by weight of the ink.

The following examples illustrate the invention more fully, however, they are not intended to limit the scope of the invention and numerous variations will be evident to those skilled in the art. In this specification, and the following examples, all parts, ratios and percentages are on a weight basis unless otherwise indicated.

EXAMPLE 1

Benzophenone tetracarboxylic dianhydride in an amount of 24.58 parts by weight (76.3 mmole) is mixed with 52.3 parts by weight (152.6 mmole) of caprolactone-2-hydroxyethyl acrylate adduct supplied by Union Carbide Corporation under the tradename TONE M-100, 0.76 parts by weight (6.22 mmole) of dimethylamino-pyridine, and 0.19 parts by weight of methyl hydroquinone. The mixture was stirred vigorously, sparged with dry air and gradually heated to 80° C. An initial exotherm of about 10° C. was noticed. A portion of the benzophenone tetracarboxylic dianhydride appeared to be undissolved. The mixture was then heated to 110° C. to 120° C. in about 30 minutes. The undissolved material then dissolved and the solution cleared to a dark orange color. The acid value of the product should be from 80 to 95 meq/g KOH. Heating is discontinued and 22.17 parts by weight of hexanediol diacrylate is added with stirring until the solution is again homogeneous. The product is then cooled. The composition is drawn down on paper to effect a 1 mil dry film thickness and photocured.

EXAMPLE 2

Example 1 is repeated with the exception that triethylamine is substituted on an equimolar basis for the dimethylamino-pyridine and the diacrylate of the two mole ethoxylate of hexanediol is substituted for the hexanediol diacrylate.

What is claimed is:

1. A compound having the formula:

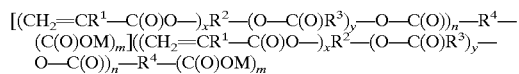

wherein:
R$^1$ is hydrogen or methyl,
R$^2$ is an alkylene group or substituted alkylene group,
R$^3$ is an alkylene group or substituted alkylene group,
R$^4$ is an aromatic radical,
M is hydrogen or a counter-ion of a salt of said compound,
n and m are integers from two to four,
x is an integer from one to three,
and y is an integer from one to five.

2. The compound of claim 1 wherein R$^4$ is a residue of a compound selected from the group consisting of polycarboxylic polyanhydrides of aromatic compounds.

3. The compound of claim 1 wherein R$^4$ is an aromatic ketone radical.

4. The compound of claim 1 wherein R$^4$ is a radical selected from the group consisting of phenyl, substituted phenyl, phenonyl, and substituted phenonyl.

5. The compound of claim 1 wherein R$^4$ has from about 6 to about 13 carbon atoms.

6. The compound of claim 1 wherein R$^4$ is the residue of a member selected from the group consisting of benzene tetracarboxylic dianhydride and benzophenone tetracarboxylic dianhydride.

7. The compound of claim 1 wherein n and m are each two.

8. The compound of claim 1 wherein R$^3$ is an alkylene group having less than ten carbon atoms.

9. The compound of claim 1 wherein R$^3$ is an alkylene group having from four to six carbon atoms.

10. The compound of claim 1 wherein R$^3$ is an alkylene group having five carbon atoms.

11. The compound of claim 1 wherein R$^2$ is an alkylene group having less than six carbon atoms.

12. The compound of claim 1 wherein R$^2$ is an alkylene group having two or three carbon atoms.

13. The compound of claim 1 wherein R$^2$ is an alkylene group having two carbon atoms.

14. The compound of claim 1 wherein x is one.

15. The compound of claim 1 wherein y is from two to four.

16. The compound of claim 1 wherein y is two.

17. The compound of claim 1 wherein R$^1$ is hydrogen.

18. The compound of claim 1 wherein R$^1$ is hydrogen, R$^2$ is an ethylene group, R$^3$ is a pentamethylene group, x is one, and y is 2.

19. A compound according to claim 18 wherein R$^4$ is the residue of benzophenone tetracarboxylic dianhydride.

* * * * *

UNITED STATES PATENT AND TRADEMARK OFFICE
CERTIFICATE OF CORRECTION

PATENT NO. : 5,912,381
DATED : June 15, 1999
INVENTOR(S) : Ramesh Narayan, Miguel A. Dones, Michael McDermott It is certified that an error appears in the above-identified patent and that said Letters Patent is hereby corrected as shown below:

column 8, line 48, after "color." Insert the sentence –Heating is discontinued and 22.17 parts by weight of hexanediol diacrylate are added with stirring until the solution is again homogenous -- column 8, line 49, delete "meq/g KOH" and replace it with –mg KOH/g--.

column 8, lines 49-51, delete the sentence "Heating is discontinued and 22.17 parts by weight of hexanediol diacrylate is added with stirring until the solution is again homogenous."

Signed and Sealed this

Twenty-third Day of May, 2000

Attest:

Q. TODD DICKINSON

*Attesting Officer*      *Director of Patents and Trademarks*